US012636487B2

(12) United States Patent
Ryaby et al.

(10) Patent No.: US 12,636,487 B2
(45) Date of Patent: *May 26, 2026

(54) SYSTEMS AND METHODS FOR MUSCULOSKELETAL TISSUE TREATMENT

(71) Applicant: ORTHOFIX US LLC, Lewisville, TX (US)

(72) Inventors: James T. Ryaby, Lewisville, TX (US); Erik Waldorff, Lewisville, TX (US); Ronald Midura, Shaker Heights, OH (US); Maciej Zborowski, Bay Village, OH (US)

(73) Assignee: Orthofix US LLC, Lewisville, TX (US)

( * ) Notice: Subject to any disclaimer, the term of this patent is extended or adjusted under 35 U.S.C. 154(b) by 1089 days.

This patent is subject to a terminal disclaimer.

(21) Appl. No.: 17/587,533

(22) Filed: Jan. 28, 2022

(65) Prior Publication Data

US 2022/0176101 A1 Jun. 9, 2022

Related U.S. Application Data

(63) Continuation of application No. 16/876,759, filed on May 18, 2020, now Pat. No. 11,235,144, which is a
(Continued)

(51) Int. Cl.
*A61N 1/04* (2006.01)
*A61B 18/00* (2006.01)
(Continued)

(52) U.S. Cl.
CPC ....... *A61N 1/0464* (2013.01); *A61N 1/36014* (2013.01); *A61N 1/36034* (2017.08);
(Continued)

(58) Field of Classification Search
None
See application file for complete search history.

(56) References Cited

U.S. PATENT DOCUMENTS 6,561,968 B1 * 5/2003 Dissing .................... A61N 2/02
600/13
7,117,034 B2 10/2006 Kronberg
(Continued)

FOREIGN PATENT DOCUMENTS

DE 102010009743 9/2011
EP 2363168 2/2011

OTHER PUBLICATIONS

International Searching Authority, Notification of Transmittal of the International Search Report and the Written Opinion of the International Searching Authority or the Declaration—mailed Mar. 28, 2018, Application No. PCT/US2018/013527, 9 Pages.
(Continued)

*Primary Examiner* — Charles A Marmor, II
*Assistant Examiner* — Marc D. Honrath
(74) *Attorney, Agent, or Firm* — Haynes and Boone, LLP

(57) ABSTRACT

A system and method for pulsed electromagnetic fields (PEMF) tissue engineering enhances musculoskeletal tissue stimulation. A tissue engineering device may include both low and high pulse frequency signal generation components that may alternatively drive one or more coils to generate PEMFs. These PEMFs may be applied to bone tissue, tendons, ligaments, and/or cartilage. A prescribed treatment regimen using the tissue engineering device may include a first period of time where a first pulse frequency is used in treatment that supports tissue proliferation followed by a second period of time where a second pulse frequency (less than the first pulse frequency) is used in treatment that supports tissue differentiation. A treatment regimen may also include, with the frequency characteristic, applying a slew rate to the pulse characteristics that is on the order of around 30 to 100 Tesla per second to drive tissue differentiation in a targeted manner.

20 Claims, 8 Drawing Sheets

Related U.S. Application Data continuation of application No. 15/870,352, filed on Jan. 12, 2018, now Pat. No. 10,653,881.

(60) Provisional application No. 62/445,882, filed on Jan. 13, 2017.

(51) Int. Cl.

| | |
|---|---|
| *A61N 1/36* | (2006.01) |
| *A61N 2/02* | (2006.01) |
| *A61N 7/02* | (2006.01) |

(52) U.S. Cl.
CPC ................. *A61N 2/02* (2013.01); *A61N 7/02* (2013.01); *A61B 2018/00005* (2013.01); *A61B 2018/0044* (2013.01); *A61B 2018/00565* (2013.01); *A61B 2018/00791* (2013.01); *A61N 1/0452* (2013.01)

(56)                References Cited

U.S. PATENT DOCUMENTS

| | | | |
|---|---|---|---|
| 7,951,061 B2 | 5/2011 | Foreman et al. | |
| 8,137,258 B1 | 3/2012 | Dennis et al. | |
| 8,376,925 B1 | 2/2013 | Dennis et al. | |
| 8,795,147 B1 | 8/2014 | Goodwin et al. | |
| 9,079,029 B2 * | 7/2015 | Weinstock | A61B 5/055 |
| 10,653,881 B2 | 5/2020 | Ryaby et al. | |
| 11,235,144 B2 * | 2/2022 | Ryaby | A61N 1/36034 |
| 2005/0049689 A1 * | 3/2005 | Gray | A61L 31/022 |
| | | | 600/431 |
| 2009/0082613 A1 | 3/2009 | Dennis et al. | |
| 2009/0287036 A1 * | 11/2009 | Shapiro | A61N 2/00 |
| | | | 600/12 |
| 2010/0249488 A1 * | 9/2010 | Kardos | A61N 2/002 |
| | | | 600/14 |
| 2014/0148870 A1 | 5/2014 | Burnett | |
| 2014/0213844 A1 | 7/2014 | Pilla et al. | |
| 2014/0342428 A1 | 11/2014 | Goodwin et al. | |

OTHER PUBLICATIONS

Australian Patent Office, Examination Report No. 1 for Standard Application, Dated Dec. 17, 2021 for Application No. 2018207572, 3 pages.
Canadian Intellectal Property Office, Examiner's Requisition, Dated Oct. 17, 2022 for Application No. 3,048,654, 3 pages.

* cited by examiner

200

Tissue Engineering Device 104

Processor 202

Memory 204

Instructions 206

HF generator 208

LF generator 210

Coil 212

Transceiver 214

Antenna 216

Sensor(s) 218

SYSTEMS AND METHODS FOR MUSCULOSKELETAL TISSUE TREATMENT

CROSS REFERENCE TO RELATED APPLICATIONS

The present application is a continuation of U.S. Non-Provisional patent application Ser. No. 16/876,759, filed May 18, 2020, which is a continuation of U.S. Non-Provisional patent application Ser. No. 15/870,352, filed Jan. 12, 2018, and issued as U.S. Pat. No. 10,653,881 on May 19, 2020, which claims priority to, and the benefit of, U.S. Provisional Patent Application No. 62/445,882, filed Jan. 13, 2017, each of which is hereby incorporated by reference in their entirety as if fully set forth below in its entirety and for all applicable purposes.

TECHNICAL FIELD

The present description relates to systems, apparatus, and methods of tissue engineering involving devices and treatment regimens to enhance the growth of musculoskeletal tissues.

BACKGROUND

An approach to treating various types of musculoskeletal issues involves applying specifically controlled pulsed electromagnetic fields (PEMF) to areas of the body where the musculoskeletal issues exist. PEMF involves low-energy, time-varying pulses of magnetic fields. PEMF can be therapeutic to various issues including bone fractures, spinal fusion, and osteoporosis as just a few examples. Specific forms of PEMF have been clinically observed to benefit in stimulating tissue differentiation and/or tissue generation when performed according to prescribed measures (i.e., duration of treatment per use, intensity of treatment, number of uses over time, etc.).

Some forms of PEMF treatments have been limited to indications for osteogenesis. However, there are many other types of injuries in need of therapeutic treatment such as that provided by PEMF, such as tendon and cartilage injuries (e.g., rotator cuff injuries, Achilles tendon injuries, etc.). Thus, there are several other indications for treatments of other injuries that are not currently available with PEMF and related treatment types.

BRIEF DESCRIPTION OF THE DRAWINGS

The present disclosure is best understood from the following detailed description when read with the accompanying figures.

DETAILED DESCRIPTION

Figure 1:
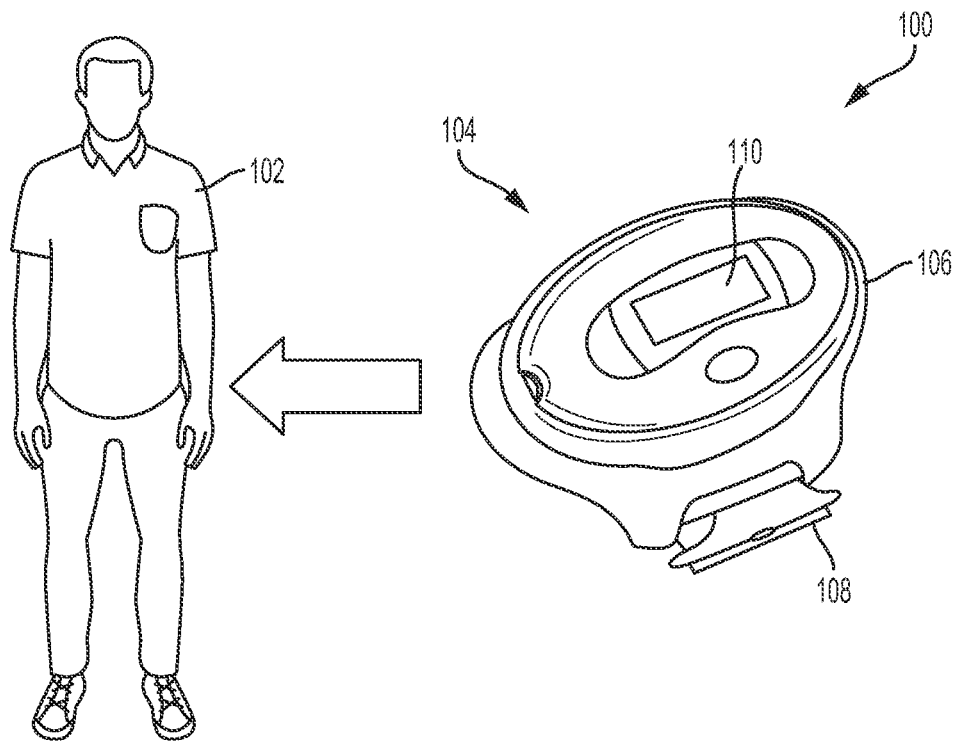
FIG. 1 is an exemplary environment for musculoskeletal tissue engineering according to aspects of the present disclosure.

All examples and illustrative references are non-limiting and should not be used to limit the claims to specific implementations and embodiments described herein and their equivalents. For simplicity, reference numbers may be repeated between various examples. This repetition is for clarity only and does not dictate a relationship between the respective embodiments. Finally, in view of this disclosure, particular features described in relation to one aspect or embodiment may be applied to other disclosed aspects or embodiments of the disclosure, even though not specifically shown in the drawings or described in the text.

Various embodiments include systems, methods, and machine-readable media for enhancing tissue engineering to a variety of tissues of a patient for a variety of indications. A tissue engineering device may include both low and high frequency signal generation components that may alternatively drive one or more coils to generate pulsed electromagnetic fields (PEMFs). These PEMFs may be applied to bone tissue, tendons, ligaments, and/or cartilage. The one or more coils may be suitably fixed or integrated with the tissue engineering device, or independently configured with communication and signal generation achieved wirelessly or in a wired configuration.

For example, in some embodiments of the present disclosure, a prescribed treatment regimen using the tissue engineering device may include a first period of time where a first pulse frequency is used in treatment that supports tissue proliferation. For example, the first pulse frequency may be a high frequency relative to the pulse frequency used for supporting tissue differentiation after aiding in proliferation. The treatment regimen may include a second period of time after the first period of time, where a second pulse frequency is then used in the treatment that supports the tissue differentiation. For example, the second pulse frequency may be a low frequency relative to the first pulse frequency—i.e., it is less than the first pulse frequency.

Given the different characteristics of the two pulse frequencies, various other treatment parameters vary between the two as well. For example, at the high pulse frequency, a treatment duration per periodic application (e.g., per day) may be multiple hours, e.g. 5 to 7. As another example, at the low pulse frequency, a treatment duration per periodic application may be less than an hour to greater than an hour, e.g. 50 minutes to 90 minutes. Transitioning between the high and low pulse frequencies may occur on a schedule, a counter (e.g., how many times the device has been energized at the pulse frequency, etc.), or alternatively may be based on data obtained from sensor measurements of the treated area (e.g., status of healing determined from the sensor data). Further, with either high or low pulse frequencies, different slew rates may be used. For example, at the low pulse or the high pulse frequency, the slew rate may be on the order of approximately 30 to 100 Tesla/second. This may correspond to a higher amplitude of the pulses at either high or low frequency, versus lower slew rates (e.g., on the order of 10 Tesla/second) due to a lower amplitude of the pulses at either the high or low frequencies.

In other embodiments, the treatment of an indication, e.g. rotator cuff repair, may occur with a low pulse frequency at the shorter duration (e.g., 50 to 90 minutes), which is in contrast to prior approaches for bone healing that typically are on the order of 3 or more hours. Alternatively, repair may occur with a high pulse frequency for between 5 to 7 hours per periodic application.

As a result of implementing the above-described approach, embodiments of the present disclosure improve the field of pulsed electromagnetic field therapy for tissue engineering, such as for tissue differentiation and/or tissue proliferation. In particular, embodiments of the present disclosure improve the efficacy of PEMF treatment for different indications beyond merely bone growth stimulation, and further that the PEMF treatment may be achieved via a combination of high pulse frequency PEMF (for proliferation) and low pulse frequency PEMF (for differentiation) in a manner that better promotes healing in a patient.

FIG. 1 illustrates an exemplary environment 100 for musculoskeletal tissue engineering according to aspects of the present disclosure. In the environment 100, a patient 102 may apply a tissue engineering device 104 to some tissue of the body of the patient 102 for therapeutic effect for one or more indications.

The tissue engineering device 104 may be a PEMF device. The tissue engineering device 104 may include a main housing 106 that includes the control, interface 110, and coil components and one or more connecting structures 108 (e.g., one or more straps to assist in applying the main housing 106 to the patient 102). The tissue engineering device 104 provides therapeutic treatment (e.g., PEMF) to musculoskeletal tissues of the patient 102.

As used herein, musculoskeletal tissue may refer to any of a variety of tissues of a patient, including bone tissue, tendons, cartilage, etc., and/or some combination thereof. In addition to an ability to provide specific treatment in osteogenesis settings such as to fractures of bones of a patient, as an adjunctive treatment option for cervical fusion, or spinal fusion (as just a few examples), the tissue engineering device 104 may further provide treatment to other tissues such as tendons like rotator cuffs and Achilles tendons of the patient 102.

According to embodiments of the present disclosure, the tissue engineering device 104 may be designed and/or configured for treating a variety of indications, including for tendenogenesis, ligamatogenesis, and/or chondrogenesis. For example, the tissue engineering device 104 may include the capability to generate two different frequencies at different periods of a treatment regimen. For example, the tissue engineering device 104 may include a prescribed treatment regimen that is stored (e.g., either pre-configured from a plurality of treatment regimen options, or dynamically entered by a user such as the patient 102, a representative of the physician (or the physician, or transmitted thereto) for the patient 102.

The prescribed treatment regimen including two different frequencies may include a first portion that has a high pulse frequency parameter, e.g. higher than the second, lower pulse frequency parameter. For example, the high frequency parameter may be on the order of tens of kilohertz. The low pulse frequency parameter may be on the order of a few kilohertz. Further, the burst frequency for treatment may be on the order of hertz, i.e. the repetition of pulse frequency treatment over time in a given treatment session (e.g., 5 to 15 hertz). The first portion and the second portion, each, of the prescribed treatment regimen may further include a periodicity of treatment (e.g., daily), a duration for each application (e.g., several hours, such as 6 to name an example), and a total duration of treatment under the first portion of the regimen (e.g., approximately 8 weeks at the high pulse frequency for someone aged 50+, or approximately 4 weeks for someone aged closer to 35, whether younger or older than that, as just some examples; generally, treatment may occur over several months, for example around 6 months).

Further, the tissue engineering device 104, whether configured for multiple pulse frequencies of treatment or not, may be configured to provide therapeutic treatment to rotator cuff tears (e.g., in a configuration that can provide multiple pulse frequencies for the PEMF, a treatment regimen may be implemented specifically for rotator cuff indications). For example, a prescribed treatment regimen may include a pulse frequency parameter on the order of a few kilohertz, a burst frequency per treatment, a periodicity of treatment (e.g., daily), a duration for each application, and a total duration of treatment over time. For example, the duration may be limited to a duration or time on the order of 60 to 90 minutes per periodic treatment. In contrast, prior approaches typically are on the order of 3 or more hours. The tissue engineering device 104 may be further configured to attach to a boot for application to an Achilles' tendon tear treatment.

As another alternative, the tissue engineering device 104, whether configured for multiple pulse frequencies of treatment or not, may be configured to provide therapeutic treatment to rotator cuff tears at a high pulse frequency, e.g. on the order of tens of kilohertz. The prescribed treatment regimen for rotator cuff tears at high pulse frequency may also include a burst frequency per treatment, a periodicity of treatment (e.g., daily), a duration for each application, and a total duration of treatment over time. For example, at high pulse frequency the duration may be on the order of six hours per periodic treatment, with a given burst frequency such as on the order of 5 to 15 hertz.

Treatment regimens may be provided to the tissue engineering device 104 for the patient 102 via entry to an interface of the tissue engineering device 104 directly, or via wireless or wired transmission. For example, a physician providing the treatment regimen for a patient using a tissue engineering device 104 may enter the prescribed treatment regimen at a portal provided by a server. In such embodiments, the physician (or someone associated with the physician) may modify existing treatment regimens according to a change in prescription.

Figure 2:
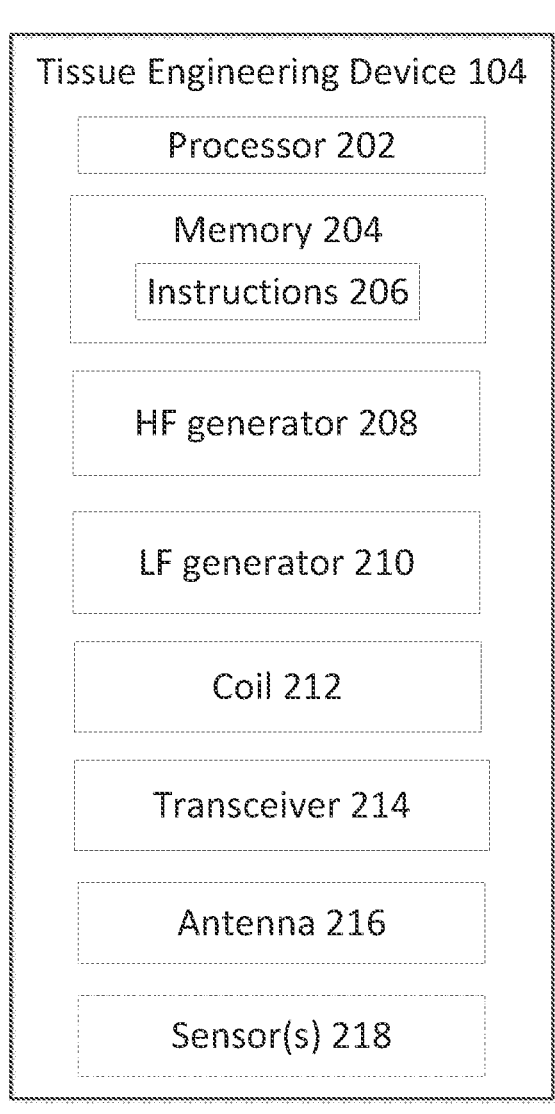
FIG. 2 is an organizational diagram of an exemplary tissue engineering device according to aspects of the present disclosure.

Turning now to FIG. 2, an organizational diagram of an exemplary tissue engineering device 104 as introduced in FIG. 1 is illustrated according to aspects of the present disclosure. In the example of FIG. 2, the tissue engineering device 104 may be a PEMF device having one of many configurations, depending upon the configuration for a desired indication as discussed further with respect to other figures below. The tissue engineering device 104 may include a processor 202, a memory 204, a high frequency pulse generator 208, a low frequency pulse generator 210, a coil 212, a transceiver 214, an antenna 216, and optionally one or more sensors 218. These elements may be in direct or indirect communication with each other, for example via one or more buses.

The processor 202 may have various features as a specific-type processor. For example, these may include a central processing unit (CPU), a digital signal processor (DSP), an application-specific integrated circuit (ASIC), a controller, a field programmable gate array (FPGA) device, another hardware device, a firmware device, or any combination thereof configured to perform the operations described herein with reference to the tissue engineering devices 104 introduced in FIG. 1 above. The processor 202 may also be implemented as a combination of computing devices, e.g., a combination of a controller and a microprocessor, a plurality of microprocessors, one or more microprocessors in conjunction with a DSP core, or any other such configuration.

The memory 204 may include a cache memory (e.g., a cache memory of the processor 202), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In some embodiments, the memory 204 may include a non-transitory computer-readable medium. The memory 204 may store instructions 206. The instructions 206 may include instructions that, when executed by the processor 202, cause the processor 202 to perform operations described herein with reference to a tissue engineering device 104 in connection with embodiments of the present disclosure, including treatment regimens (e.g., treatment parameters including pulse frequency or frequencies to apply, burst frequency, total duration of treatment for the regimen, an amount of treatment on a given periodic basis such as daily, etc.). The terms "instructions" and "code" may include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The high frequency pulse generator 208 is configured to generate the current and/or voltage sent to the coil 212 to generate the PEMF according to the treatment regimen (e.g., pulses). For example, the processor 202 may generate a command to generate a pulse (e.g., a train of pulses) that is sent to the high frequency generator 208. The high frequency pulse generator 208, in turn, responds to the command with the current according to the pulse frequency setting specified in the treatment regimen (e.g., on the order of tens of kilohertz, such as between 35 and 50 kilohertz to name an example). The current from the high frequency pulse generator 208 may be in a form that results in the coil 212 generating a quasi-rectangular pulse as a ratio of change in amplitude of a magnetic field to a time to make the change in amplitude (i.e., dB/dt—the ratio of change in amplitude of the B field (magnetic field) (dB) to the time taken to achieve that change in amplitude (dt)). The quasi-rectangular pulse may be, for example, determined by a Fourier transform of a sinusoidal signal. In the B spectrum, this quasi-rectangular pulse becomes a rectangular waveform.

Figure 3:
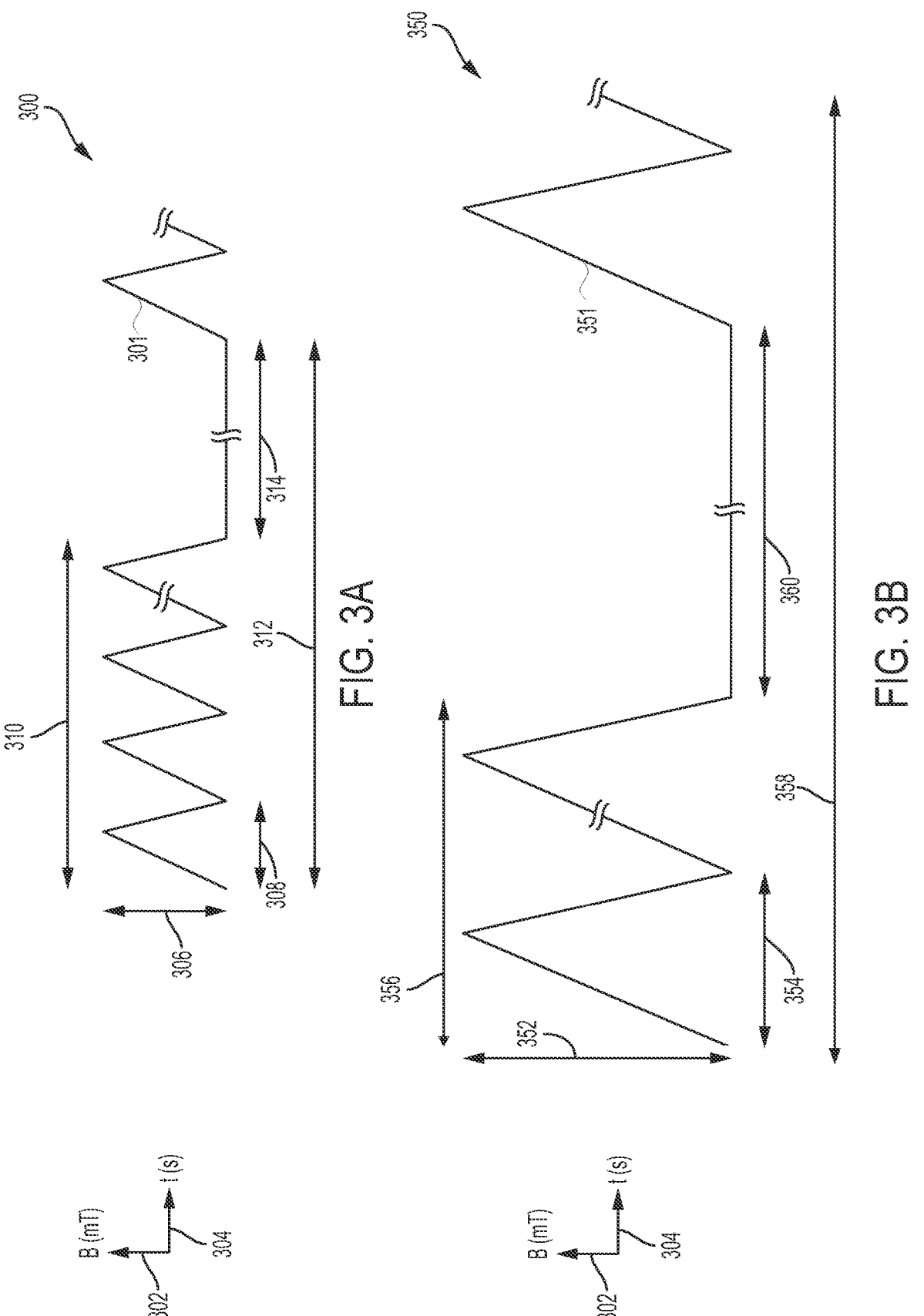
FIG. 3A is an exemplary diagram of signal characteristics according to aspects of the present disclosure.
FIG. 3B is an exemplary diagram of signal characteristics according to aspects of the present disclosure.

An example of the output from the high frequency pulse generator 208 is illustrated in FIG. 3A, which is an exemplary diagram 300 of signal characteristics according to aspects of the present disclosure. The signal 301 is illustrated with the axis 302 representing the magnetic field (e.g., in milliTesla units) and the axis 304 in time (e.g., in milliseconds). The amplitude 306 of the signal 301 may be on the order of 0.1 milliTesla (mT), e.g. 0.095 mT, plus or minus approximately 0.05 mT. As a result, for example, a total amount of energy delivered to tissue may be sufficiently low that notable heating of the tissue is avoided (e.g., above a threshold temperature of a few degrees, for example). The slew rate according to the above characteristics may be on the order of around 20 Tesla/second. In other examples, the amplitude 306 of the signal 301 may be on the order of several mT, e.g. 10 mT plus or minus 4 mT. With the same pulse width as the lower amplitude examples, the slew rate of the higher-amplitude 306 alternative may be on the several times larger than the slew rate of the lower-amplitude 306.

The pulse width 308 may be approximately 24 microseconds, with a number of pulses 310 in a given burst 312 (e.g., approximately 21 pulses in a burst for example) resulting in the high pulse frequency. Further, the burst 312 may include both the pulses 310 as well as a latent period 314 (e.g., some dozen of milliseconds, such as approximately 60 to 70 milliseconds as an example). For example, the burst frequency of the bursts 312 may be on the order of hertz, for example between 5 and 15 hertz (though other ranges are possible as well). With these example characteristics, the high pulse frequency may be between 35 and 50 kilohertz, such as around 40 kilohertz (40.85 kHz as one particular example). This higher pulse frequency for the PEMF can drive tissue proliferation in targeted areas of tissue, whether that be for osteogenesis, tendenogenesis, ligamatogenesis, and/or chondrogenesis.

Returning to FIG. 2, the low frequency pulse generator 210 is configured to generate the current and/or voltage sent to the coil 212 to generate the PEMF according to a low-frequency pulse treatment regimen. For example, in response to the processor 202 generating a command for the low frequency pulse generator 210 to generate a low frequency pulse (e.g., a train of pulses at the pulse frequency), the low frequency pulse generator 210 may provide current according to the pulse frequency setting specified in the treatment regimen for low pulse frequency PEMF (e.g., on the order of a few kilohertz, such as approximately between 2 and 6 kilohertz to name an example). The current from the low frequency pulse generator 210 may be in a form that results in the coil 212 generating a quasi-rectangular pulse as well, for example, determined by a Fourier transform of a sinusoidal signal (in the dB/dt spectrum, or a rectangular waveform in the B field spectrum).

In some embodiments, the high frequency pulse generator 208 and the low frequency pulse generator 210 may be implemented as part of physically separate circuits (e.g., separate printed circuit boards), as different circuits on the same circuit board, or fully integrated together as will be recognized. Further, in some embodiments the coil 212 may include multiple different coils, including one to generate low frequency pulses from the current provided by the low frequency pulse generator 210, and another one to generate high frequency pulses from the current provided by the high frequency pulse generator 208. Alternatively, the coil 212 may be one shared coil used to generate pulses for each of the high and low frequency pulse generators 208/210.

An example of the output from the low frequency pulse generator 210 is illustrated in FIG. 3B, which is an exemplary diagram 350 of signal characteristics according to aspects of the present disclosure. The signal 351 is illustrated with an amplitude 352. In an embodiment, the amplitude 352 may have a magnitude on the order of several of mT, e.g. 10 mT plus or minus 4 mT. In such embodiments, the pulse width 354 may be on the order of several hundred microseconds, such as approximately 260 microseconds. There may be a number of pulses 356 in a given burst 358 (e.g., approximately 21 pulses in a burst for example).

Further, the burst 358 may include both the pulses 356 as well as a latent period 360 (e.g., some dozen of milliseconds, such as approximately 60 to 70 milliseconds as an example). With these example characteristics, the low pulse frequency may be between 2 and 6 kilohertz, such as around 5 kilohertz (3.85 kilohertz as one particular example). The burst frequency of the bursts 358 may be between 10 and 20 hertz, such as around 15 hertz (though other ranges are possible as well). Further, the slew rate according to the above characteristics may be on the order of approximately 100 Tesla/second (e.g., 30-100 T/s), which relative to other slew rates in use may be notably larger, such as an order of magnitude larger (e.g., 10 T/s) than prior approaches. This lower pulse frequency for the PEMF can drive tissue differentiation in targeted areas of tissue, whether that be for osteogenesis, tendenogenesis, ligamatogenesis, and/or chondrogenesis.

As another example with respect to amplitude 352, the signal 351 of FIG. 3B may have an amplitude of approximately 0.1 mT, plus or minus 0.05 mT. The pulse frequency may again be low relative to the high pulse frequency, e.g. again on the order of approximately 2 to 6 kilohertz. As can be seen, therefore, between FIGS. 3A and 3B, the high pulse frequency signal is "high" in that it is higher in pulse frequency that the low pulse frequency signal. Further, in FIG. 3B with the lower amplitude characteristics and the same pulse width 354, the corresponding slew rate is therefore lower (e.g., on the order of 10 T/s).

Returning again to FIG. 2, the coil 212 provides PEMF pulses according to embodiments of the present disclosure. The coil 212 may be constructed with multiple windings of any suitable material for generating electromagnetic fields according to the treatment regimen as provided by the processor 212 to the high frequency pulse generator 208 and/or low frequency pulse generator 210. For example, the processor 202 may access the treatment regimen stored in the memory 204 that identifies a set rise and/or fall time, duty cycle, amplitude, pulse frequency, burst frequency, slew rate, etc. The processor 202 then sends the appropriate commands to the applicable generator—the high frequency pulse generator 208 for high pulse frequency PEMF treatment portions and/or the low frequency pulse generator 210 for low pulse frequency PEMF treatment portions. The applicable generator then causes current to pass through the coil 212, so as to generate electromagnetic frequency pulses of a desired duration, size, shape, and frequency according the commands' treatment regimen.

As noted above, the treatment regimen may include programmed pulse trains, where each pulse train includes a specified number of pulses with specified duration (and rise/fall times with specified amplitude) for a specified pulse frequency, and repeated in a fixed pattern over time (i.e., duty cycle) over the course of a given treatment period (therefore, at a specified burst frequency over the given treatment period). There may be a number of treatment periods specified over a longer duration of time. For example, a given treatment period may be specified to last for tens of minutes to several hours each day, which may be repeated for a longer duration such as over weeks or months, or a specified number of treatments. A heartbeat LED may indicate a treatment status for the periodic application of the PEMF over the long-term duration.

The tissue engineering device 104 may further include the transceiver 214. The transceiver 212 may be configured to communicate bi-directionally with other devices, such as network elements in communication with a back-end server, i.e. an interface with a treating physician, mobile devices (such as tablets, cell phones, etc.), and/or other tissue engineering devices 104. The transceiver 214 may do so by providing modulated and/or processed data, e.g. data packets (or, more generally, data messages that may contain one or more data packets and other information), to the antenna 216 for transmission to one or more other devices. The antenna 216 may further receive data messages transmitted from other devices and provide the received data messages for processing and/or demodulation at the transceiver 214. Although FIG. 2 illustrates antenna 216 as a single antenna, antenna 216 may include multiple antennas of similar or different designs in order to sustain multiple transmission links.

For example, the transceiver 214 may be a Bluetooth low energy (BLE) device. In other embodiments, the transceiver 212 may be a USB port, an Ethernet port, a cell module (e.g., LTE, 5G, etc.), a WiFi module, a ZigBee module, or a near field communication (NFC) module. The tissue engineering device 104 may further include multiple transceivers 214 to optionally communicate with different devices concurrently.

The tissue engineering device 104 may further include one or more sensors 218. These may be any number of sensors that may monitor different aspects of operation of the tissue engineering device 104. For example, the tissue engineering device 104 may include an impedance monitor sensor (also referred to as simply an impedance monitor). The impedance monitor may use impedance spectroscopy to identify different types of tissue of the patient and correlate that to the known types of tissues present in the different stages of healing. This data may be included to assist in monitoring the progress of healing. The impedance monitor may be an ultrasound or electromagnetic field.

As an alternative to the impedance monitor sensor, more generally the impedance monitor sensor may be a type of sensor to monitor healing. This may include an impedance monitor sensor as noted above. Alternatively, it may include a sensor such as x-rays (e.g., low-energy x-rays), ultrasound, electrical impedance tomography, or other approaches to measure healing or density such as measuring electrical and/or electroacoustic properties of healing tissue, etc. (e.g., some combination of the above sensor types). All of these approaches may be referred to herein generically under "tissue monitoring" and "impedance monitoring sensors" for purposes of simplicity.

In some embodiments, the data may be used to estimate the progress of healing in embodiments where both high pulse frequency and low pulse frequency portions are included in a prescribed treatment regimen. For example, once data from the impedance monitor identifies predicted healing above a first impedance threshold (e.g., set by the physician or previously based on clinical trial results), the tissue engineering device 104 may transition from a first portion of the treatment regimen—such as a high pulse frequency treatment portion—to a second portion of the treatment regimen that uses a low pulse frequency treatment.

Other examples of sensors may include other suitable options, including accelerometers, infrared sensors, global positioning system, or some combination thereof to name just a few examples.

Another example of sensors may include a timer. For example, the timer may track a total amount of time that the tissue engineering device 104 has been in use for a given treatment regimen. This may occur, for example, from storing a beginning date (and time, in some embodiments) that treatment begins for a selected treatment regimen, and logging each subsequent date (and time in some embodiments) that the same selected treatment regimen is thereafter selected. The timer may compare, or send the tracked information to the processor 202 for comparison, the duration of the treatment regimen actually being applied (e.g., by determining a difference between the current date and the beginning date, or some finer granularity based on tracked time periods for each application of the treatment on each day, etc.) to the specified total duration in the treatment regimen.

As another example, the timer may track an amount of time the coil 212 is energized and log that over multiple applications of treatment according to the treatment regimen, and comparison may be made (e.g., by the timer or the processor 202) of the total treatment time (over the multiple applications) against a threshold treatment time.

Alternatively, the timer may be a counter that counts a total number of times that the coil 212 is energized. This count may be compared, by the counter or by the processor 202, for example, against a threshold count specified in the treatment regimen. The result under either approach (e.g., timer or counter) may be to assist the tissue engineering device 104 (either the processor 202 or a user of the tissue engineering device 104) to determine whether and/or when to transition from between high pulse frequency and low pulse frequency portions included in a prescribed treatment regimen. For example, once data from the timer/counter exceeds a first threshold (e.g., set by the physician or previously based on clinical trial results), the tissue engineering device 104 may transition from a first portion of the treatment regimen—such as a high pulse frequency treatment portion—to a second portion of the treatment regimen that uses a low pulse frequency treatment. As another example, once data from the timer/counter falls below a second threshold, the tissue engineering device 104 may transition from a second portion (e.g., low pulse frequency) to a first portion (e.g., high pulse frequency).

Figure 4:
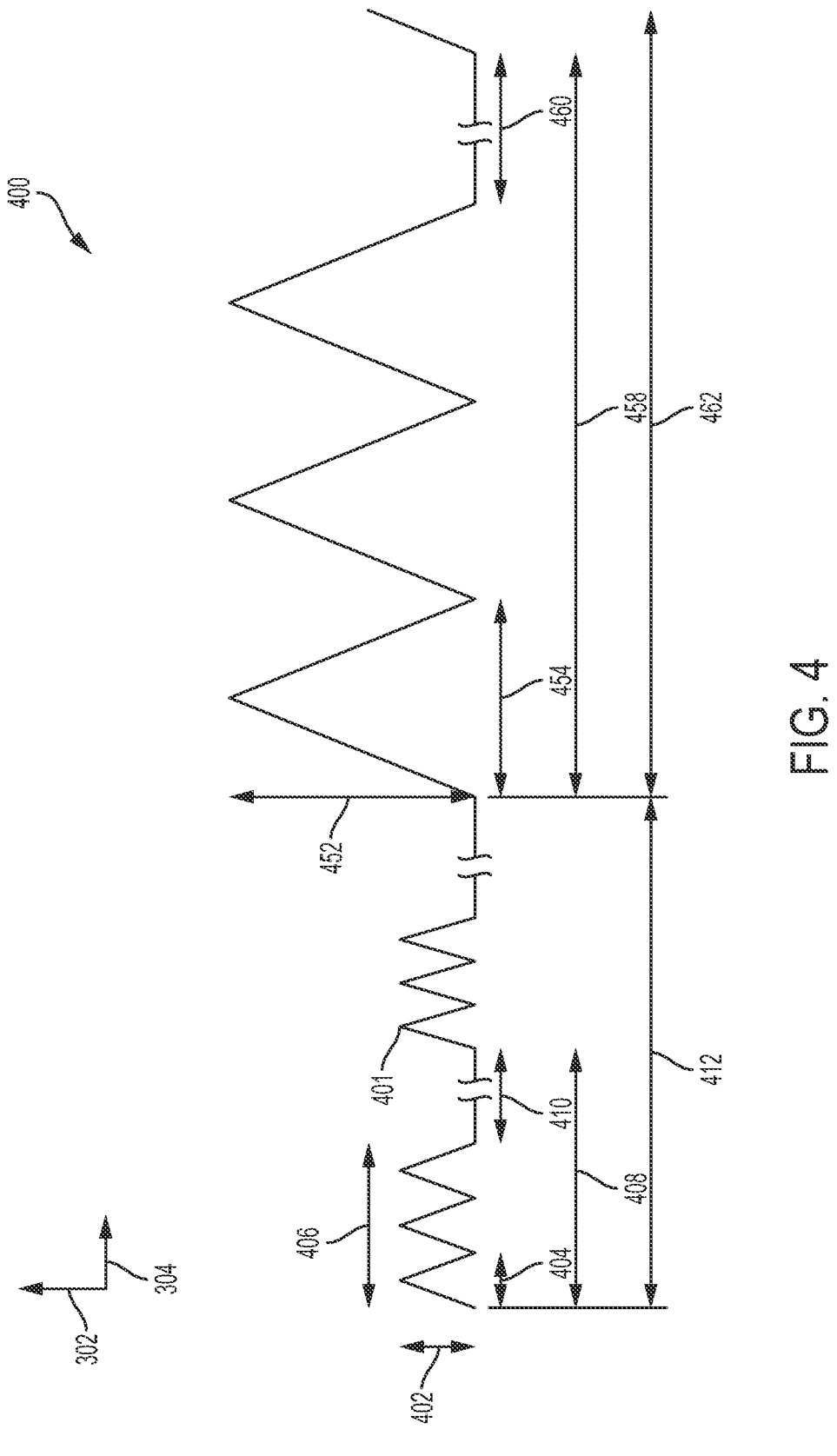
FIG. 4 is an exemplary diagram of signal characteristics according to aspects of the present disclosure.

Turning now to FIG. 4, an exemplary diagram 400 of signal characteristics according to aspects of the present disclosure is illustrated. In particular, the diagram 400 illustrates a treatment regimen with two portions as touched on with respect to the previous figures—for example, a first portion 412 at a first pulse frequency and a second portion 462 at a second pulse frequency. In some embodiments, the first portion 412 constitutes a high pulse frequency portion and the second portion 462 constitutes a low pulse frequency portion. Further, the first portion 412 may constitute a first slew rate and the second portion 462 may constitute a second slew rate, for example where the first slew rate (e.g., as a high pulse frequency portion) may have a lower slew rate than the second slew rate (e.g., as a low pulse frequency portion). Alternatively, the first slew rate (for a high pulse frequency portion) may have a slew rate greater than the second slew rate (for a low pulse frequency portion), for example where the amplitude in the first portion 412 is on the order of 5-15 mT. In further examples, the pulse frequencies of each portion may be the same, e.g. a low pulse frequency, while the slew rates differ between the portions 412 and 462.

The first portion 412 15 includes a burst 408, similar to the burst 312 discussed above with respect to FIG. 3A. Within the burst 408, the signal 401 includes pulse widths 404 for each pulse within a train of pulses 406, similar to elements 308 and 310 respectively of FIG. 3A. Further, each burst 408 includes a latent period 410 similar to the latent period 314 discussed above with respect to FIG. 3A. The pulses have amplitudes 402, similar to the exemplary amplitudes 306 and exemplary slew rates of FIG. 3A. There are typically multiple bursts 408 within the first portion 412 (e.g., multiple per a given a treatment such as in a day, as well as multiple days/weeks before the second portion 462 begins).

At some point, the treatment regimen may specify that the treatment should transition from the first portion 412 to the second portion 462. This may be according to a pre-set time frame, e.g. after some specified number of weeks (e.g., depending upon the age of the patient 102). Alternatively, this may be in response to one or more sensors 218 providing data that enables the tissue engineering device 104 to determine that the stage of healing has reached a threshold.

Regardless of how the transition is triggered to occur, in the second portion 462 is included bursts 458. In a given burst 458, of which there will similarly be multiple per a given treatment day, as well as multiple days/weeks before the second portion 462 ends (e.g., either in response to a schedule expiring in the treatment regimen and/or data from the sensors reaching a second threshold). The signal 401 in the second portion 462 includes pulse widths 454 for each pulse within a train of pulses 458, similar to elements 354 and 356 respectively in FIG. 3B. Further, each burst 458 includes a latent period 460 similar to the latent period 360 discussed above with respect to FIG. 3B. The pulses 454 have amplitudes 452 that may have characteristics similar to the exemplary amplitudes 352 and exemplary slew rates discussed above with respect to FIG. 3B.

Thus, according to the signal 401 characteristics illustrated in FIG. 4, according to a treatment regimen the high frequency pulse generator 208 may, for the first portion 412 (of time, typically over multiple treatments within a multi-week timespan) generate the appropriate currents to drive the coil 212 at the target high pulse frequency when directed by the processor 202. The processor 202 may determine when it is time to transition to the second portion 462, such as in response to a user input, a setting/timer expiration/calendar date entered previously in the treatment regimen stored in the memory 204, and/or data from the sensor(s) 218, to name just a few examples.

In response, the processor 202 may cause the signal 401 to transition to the second portion 462, in which the low frequency pulse generator 210 may take over in generating the appropriate currents to drive the coil 212 when directed by the processor 202 for providing a low pulse frequency such as the examples given above. Thus, in the example of FIG. 4, during the first portion 412 the high pulse frequency characteristics of the PEMF treatment may drive tissue proliferation, after which in the second portion 462 tissue differentiation may be primarily driven by the low pulse frequency characteristics of the PEMF treatment according to the tissue's response thereto.

Figure 5:
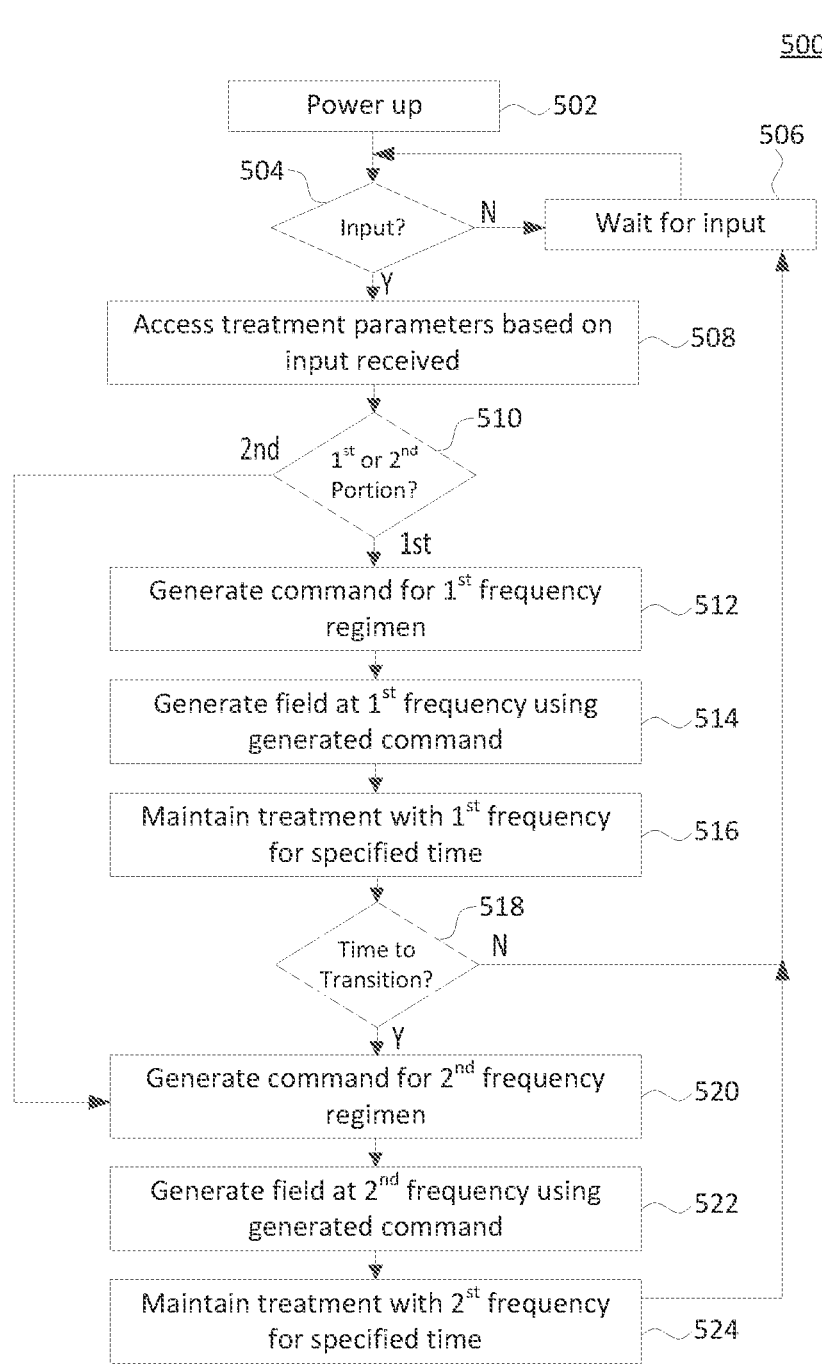
FIG. 5 is a flowchart illustrating an exemplary method for tissue treatment according to aspects of the present disclosure.

Turning now to FIG. 5, a flowchart illustrating an exemplary method 500 for tissue treatment according to aspects of the present disclosure. In particular, the method 500 illustrates aspects of operation of the tissue engineering device 104 according to embodiments of the present disclosure with respect to combined high/low pulse frequency PEMF treatment. It is understood that additional steps can be provided before, during, and after the steps of method 500, and that some of the steps described can be replaced or eliminated from the method 500.

At block 502, the tissue engineering device 104 powers up, whether from a sleep mode or from an off state, such as triggered by a user such as the patient 102 or an internal timer (e.g., set according to the prescribed treatment regimen in effect at the tissue engineering device 104).

At decision block 504, the tissue engineering device 104 determines whether it has received an input. The input may be a command entered at that time by the user of the tissue engineering device 104, e.g. via the interface 110. Alternatively, the input may be a transmission received via the antenna 216/transceiver 214. As yet another alternative, the input may be a previously-stored, scheduled instruction regarding the treatment regimen. As another alternative, the input may be sensor input data, such as from an impedance monitor, or timer/counter data from a timer or counter (e.g., as discussed above with respect to sensor(s) 218).

If it is determined at decision block 504 that no input has been received yet, then the method 500 proceeds to block 506, where the tissue engineering device 104 waits for an input. The method 500 returns in a loop to decision block 504 until an input is detected.

If it is determined at decision block 504 that an input has been received, then the method 500 proceeds to block 508.

At block 508, the tissue engineering device 104 accesses one or more treatment parameters based on the input detected. For example, the tissue engineering device 104 may access pulse frequency parameter, burst duration, burst frequency, number of pulses, amplitude of the pulses, rise time/slew rate of the pulses, shape of the pulses, and/or any other parameter or some combination thereof. These parameters may have been either previously stored as part of the treatment regimen in the memory 204, and/or updated via user input via the interface 110 and/or received via the transceiver 214 from some other, remote source.

At decision block 510, the tissue engineering device 104 determines the pulse frequency level of the parameters accessed for the current portion of the treatment regimen (e.g., determining whether the treatment regimen is now in the high or low pulse frequency portions of the treatment). According to embodiments of the present disclosure, the high pulse frequency treatment portion may occur first. Thus, if the schedule currently identifies treatment to be according to the first portion, that corresponds to a first pulse frequency that is a high pulse frequency (e.g., on the order of tens of kilohertz).

If high pulse frequency, the "first frequency" in FIG. 5, then the method 500 proceeds to block 512.

At block 512, the processor 202 of the tissue engineering device 104 generates the command for the high frequency pulse generator 208 to generate high pulse frequency pulses according to the first portion (e.g., 412 of FIG. 4) of the treatment regimen.

At block 514, the tissue engineering device 104's high frequency pulse generator 208 generates the PEMF (the pulses) according to the command(s) received from the processor 202 from block 512.

At block 516, the tissue engineering device 104 maintains the treatment using the first, high pulse frequency for the specified period of time. Thus, for a given periodic application of treatment according to the treatment regimen (on a given day), the tissue engineering device 104 may maintain the treatment using the first, high pulse frequency for the duration of the period.

At decision block 518, the tissue engineering device 104 determines whether the time to transition to the second period of the treatment regimen has arrived. This determination may be made based on any of a plurality of factors (or some combination thereof). For example, the determination may be based on a schedule—e.g., a timer tracking use of the tissue engineering device 104 over time in comparison to a beginning of use for the current portion of the treatment regimen. As another example, the determination may be based on a count—e.g., a counter tracking each energization of the coil 212 over time at the given pulse frequency level (within an acceptable variance of that level, for example)

and that count being compared to a specified number of times. As another example, the determination may be based on sensor data—e.g., receiving impedance monitor data and comparing that impedance monitor data to a specified threshold level (or levels) stored in a memory (or transmitted to an external, remote system for comparison to levels) to aid in a determination whether healing of the target tissue has reached a target level to transition to the other portion of the treatment regimen.

If, at decision block 518, it is determined that the time has not arrived, and the current application is complete (e.g., the duration for the given periodic treatment has been reached), then the method 500 returns to block 506 to wait for the next input, which could be from a user, a schedule in the device, a transmission, etc.

If, instead, it is determined at decision block 518 that the time to transition has arrived, then the method 500 proceeds to block 520. In some embodiments, the pulse frequency level selected at the start of the periodic application remains the same at the conclusion of the periodic application. In other embodiments, if the scheduled period of time expires for using the first, high pulse frequency or one or more sensors 218 assist in identifying a threshold as being met, then the treatment may transition to the second, low pulse frequency in the course of the current periodic application.

At block 520, the processor 202 of the tissue engineering device 104 generates the command for the low frequency pulse generator 210 to generate low pulse frequency pulses according to the second portion (e.g., 462 of FIG. 4) of the treatment regimen.

At block 522, the tissue engineering device 104's low frequency pulse generator 210 generates the PEMF (the pulses) according to the command(s) received from the processor 202 from block 520.

At block 524, the tissue engineering device 104 maintains the treatment using the second, low pulse frequency (a pulse frequency lower than the first, higher pulse frequency) for the specified period of time. Thus, for a given periodic application of treatment according to the treatment regimen (on a given day), the tissue engineering device 104 may maintain the treatment using the second, low pulse frequency for the duration of the period.

Returning to decision block 510, if it is determined that the pulse frequency level is the low, second pulse frequency level, then the method 500 proceeds to block 520 and proceeds as discussed above.

From block 524, the method 500 may return to block 506 and waiting for the next input as discussed above. Thus, in the method 500 of FIG. 5, tissue proliferation may be first driven by a high pulse frequency PEMF configuration, after which tissue differentiation may be primarily driven by the low pulse frequency PEMF configuration to achieve a more effective treatment of an indication for osteogenesis, tendenogenesis, ligamatogenesis, and/or chondrogenesis as some examples.

Figure 6:
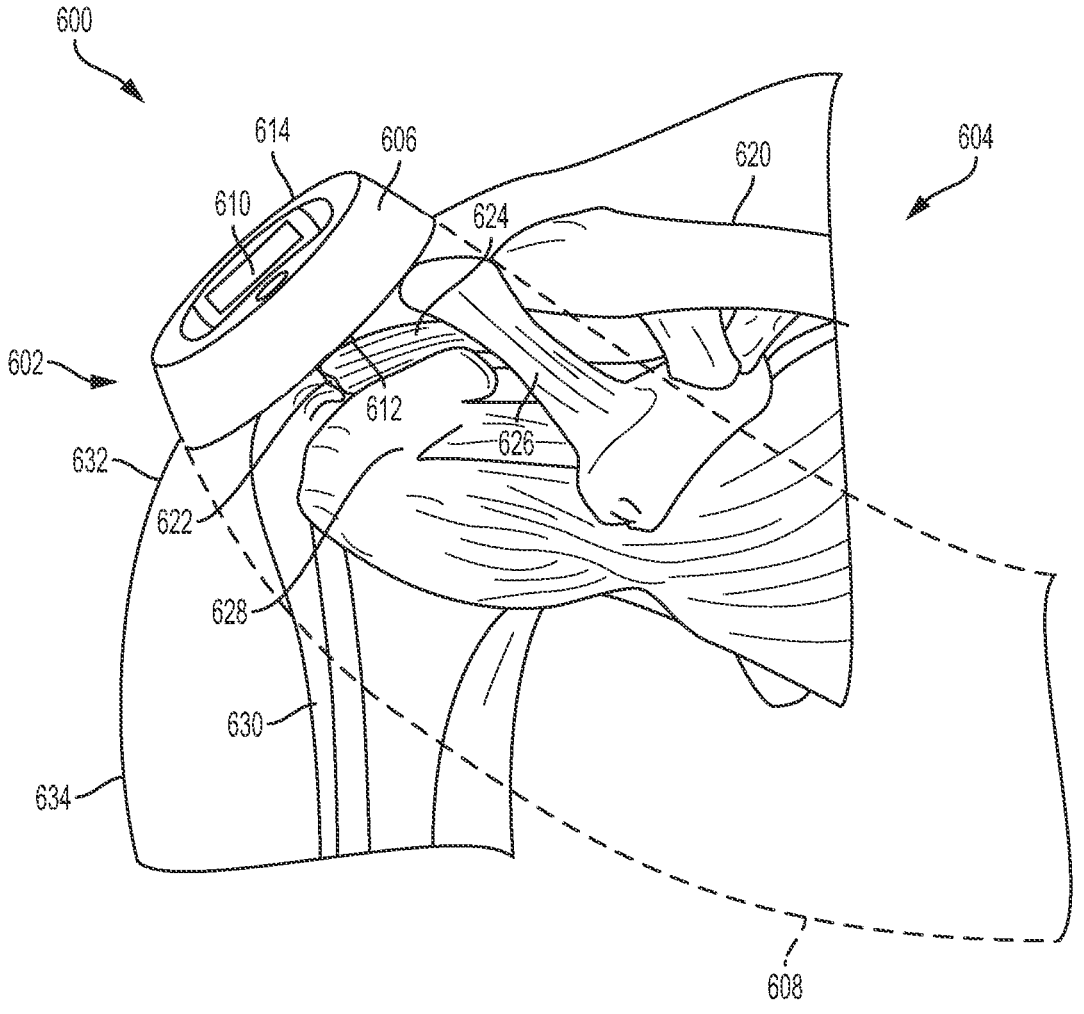
FIG. 6 is a diagram illustrating an exemplary application of a tissue engineering device according to aspects of the present disclosure.

FIG. 6 is a diagram 600 illustrating an exemplary application of a tissue engineering device 602 according to aspects of the present disclosure. The tissue engineering device 602 is an example of a tissue engineering device 104 configured for use in tendenogenesis, or more generally tendon tissue repair (e.g., including insertion point and midsubstance repairs), in particular for assisting with repairing rotator cuff injuries.

The shoulder 632 of a patient 604 is illustrated in a stylized manner in FIG. 6. As shown, a patient 604's shoulder 632 includes the arm 634, humerus 630, rotator cuff 624, rotator cuff tear 622, subscapularis tendon 628, clavicle 620, and tendon 626. The tissue engineering device 602 includes the main housing 606 and strap 608. The main housing 606 includes a bottom 612 in contact with the shoulder 632 of the patient 604 (e.g., the bottom 612 of the main housing 606 may be anatomically figured to generally conform with the shoulder 632) as well as a top 614 on which side an interface 610 is located. Coil(s) 212 (FIG. 2) may be configured external to the main housing 606 to generate PEMFs that reach the rotator cuff 624 and, particularly, the area of the rotator cuff tear 622. Alternatively, the coil(s) 212 (FIG. 2) may be configured within the main housing 606.

In the embodiment illustrated in FIG. 6, the treatment regimen programmed into the tissue engineering device 602 may be configured to provide a one of either low pulse frequency (e.g., on the order of several kilohertz) or high pulse frequency (e.g., on the order of tens of kilohertz). Alternatively, the treatment regimen may in this embodiment also include both high pulse frequency and low pulse frequency components over time. If the tissue engineering device 602 is configured according to a low pulse frequency profile (e.g., FIG. 3B with an amplitude of approximately 1 mT or 10 mT with lower slew rate as some examples), then the tissue treatment regimen may specify a unique treatment duration for each periodic application of the therapeutic signals. For example, the duration may be limited to a duration or time on the order of 30 to 120 minutes, for example 60 to 90 minutes, per periodic treatment according to some embodiments for tendenogenesis (rotator cuff repair). In contrast, prior approaches typically are on the order of 3 or more hours and are for a different indication, such as osteogenesis (bone growth stimulation).

If the tissue engineering device 602 is configured to according to a high pulse frequency profile (e.g., FIG. 3A), then the tissue treatment regimen may specify a unique treatment duration for each periodic application of the therapeutic signals at high pulse frequency. For example, the duration may be on the order of 6 hours per periodic treatment according to some embodiments for the tendenogenesis that utilize the higher pulse frequency at approximately 35 kilohertz to 50 kilohertz, such as around 40 kilohertz.

Another application of embodiments of the present disclosure may be to other tendons such as the Achilles tendon. This is illustrated in FIG. 7, which introduces a diagram 700 according to aspects of the present disclosure.

As shown, the foot of a patient 702 is in a boot 730. The boot 730 includes a base 732, a top 724, a front 734 towards where the toes 725 of the patient 702 face, a rear 736 located in a vicinity to the heel 720 of the patient 702, and (attachable to the rear 736) the tissue engineering device 704 (an example of the tissue engineering device 104 of FIGS. 1 and 2). The tissue engineering device 704 may be integrally formed with one or more parts of the boot 730 or releasably connected thereto. Further, if it is a releasable connection, then in some embodiments the location of the releasable connection may be adjusted, such as up or down with reference with the bottom 732 of the boot 730, so as to better locate the fields over the target treatment area (e.g., where the tear is located on the Achilles' tendon 722).

The tissue engineering device 704 is an example of a tissue engineering device 104 configured for use in tendenogenesis, in particular for assisting with Achilles tendon 722 injuries. The tissue engineering device 704 includes the main housing 706. The main housing 706 includes a bottom 712 and a top 714 on which side an interface 710 is located. Coil(s) 212 (FIG. 2) may be configured within the main housing 706 to generate PEMFs that reach the Achilles tendon 722, and particularly the area of the injury to the Achilles tendon (e.g., generally at a level approximate to the ankle 726 of the patient 702).

Figure 7:
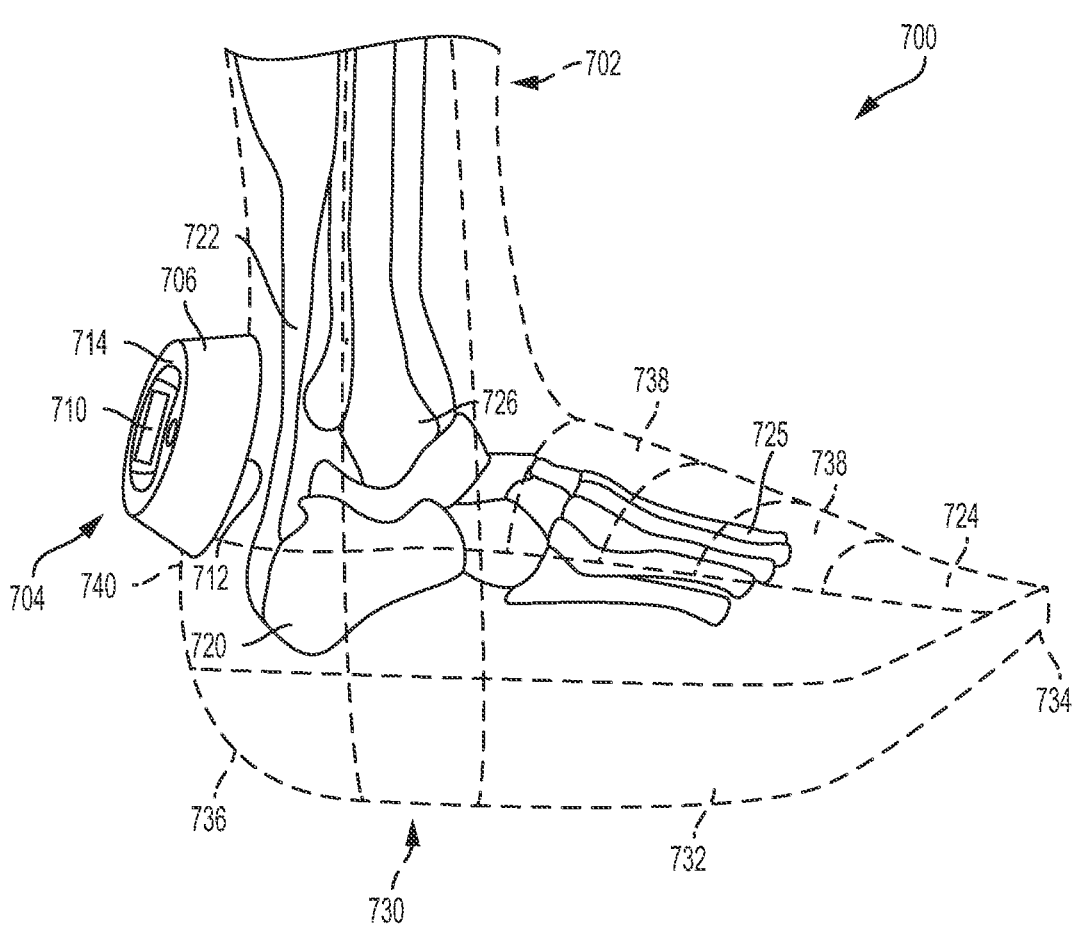
FIG. 7 is a diagram illustrating an exemplary application of a tissue engineering device according to aspects of the present disclosure.

In the embodiment illustrated in FIG. 7, the treatment regimen programmed into the tissue engineering device 704 may also be configured to provide one of either low pulse frequency, high pulse frequency, or both high and low components over time such as discussed above with respect to FIGS. 3A, 3B, and/or 4, such as discussed with respect to FIG. 6.

Figure 8:
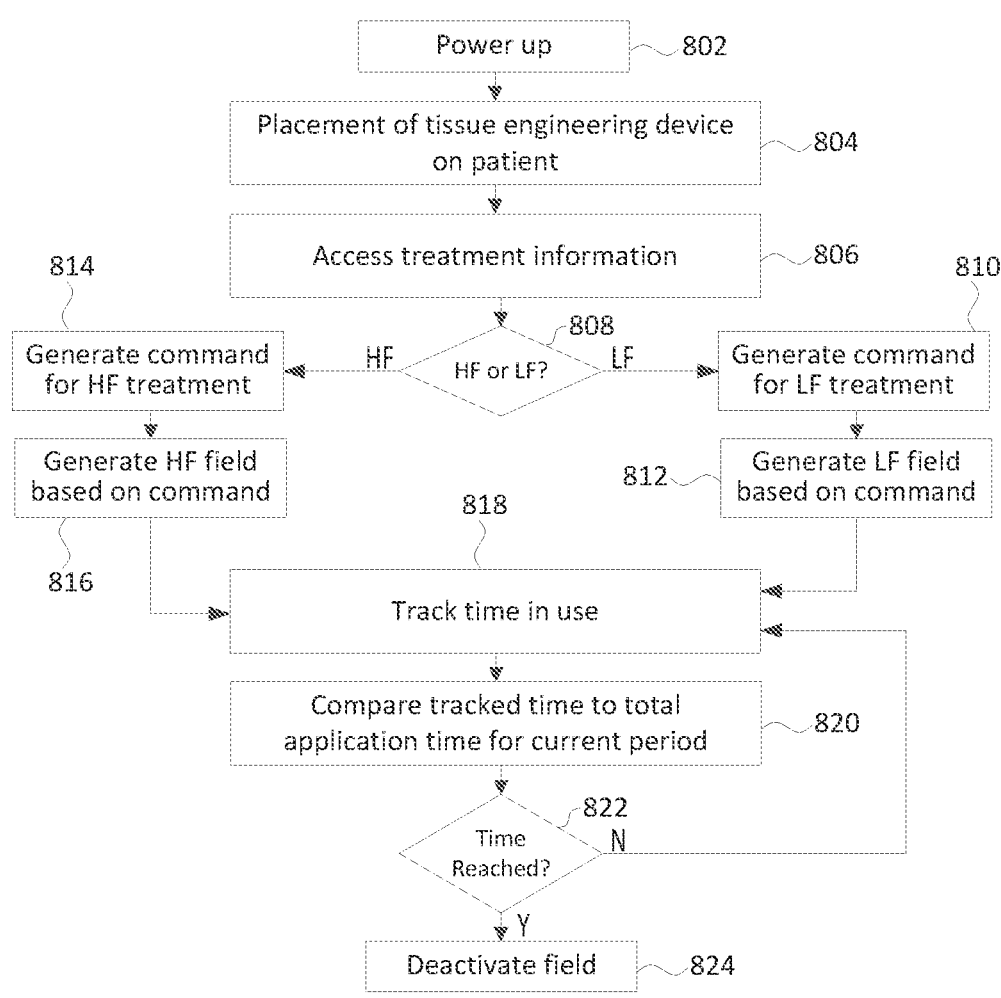
FIG. 8 is a flowchart illustrating an exemplary method for tissue treatment according to aspects of the present disclosure.

FIG. 8 is a flowchart illustrating an exemplary method 800 for tissue treatment according to aspects of the present disclosure. In particular, the method 800 illustrates aspects of operation of the tissue engineering device 602 of FIG. 6 (or the tissue engineering device 704 of FIG. 7) according to embodiments of the present disclosure with respect to combined high/low pulse frequency PEMF treatment. For simplicity of discussion, reference will be made to tissue engineering device 602 with respect to method 800. The tissue engineering devices discussed herein could additionally be used with prescribed treatment regimens with other tendons, ligaments, cartilage, etc. It is understood that additional steps can be provided before, during, and after the steps of method 800, and that some of the steps described can be replaced or eliminated from the method 800.

At block 802, the tissue engineering device 602 powers up, whether from a sleep mode or from an off state, such as triggered by a user such as the patient 102 or an internal timer (e.g., set according to the prescribed treatment regimen in effect at the tissue engineering device 104).

At block 804, the tissue engineering device 602 is placed on the patient in a relevant location, for example on the shoulder 632 directed toward the rotator cuff 624 and, specifically, the rotator cuff tear 622. As another example, the tissue engineering device 704 is attached to the boot 730 facing the location of the Achilles tendon 722.

At block 806, the tissue engineering device 602 accesses treatment information. This treatment information includes the parameters such as those discussed above—including such parameters as a pulse frequency parameter, a burst duration, a burst frequency, a number of pulses, an amplitude of the pulses, a rise time/slew rate of the pulses, a shape of the pulses, and/or any other parameter or some combination thereof. These parameters may have been either previously stored as part of the treatment regimen in the memory 204 (FIG. 2), and/or updated via user input via the interface 610 and/or received via the transceiver 214 (FIG. 2) from some other, remote source.

At decision block 808, the tissue engineering device 602 determines whether the treatment regimen specifies a high or low pulse frequency treatment. In some embodiments, the pulse frequency level of treatment may be specified as a selection at the tissue engineering device 602 between one of multiple treatment regimens stored at the tissue engineering device 602 (and/or accessible by the tissue engineering device 602 via wired or wireless connection(s)). That selection may be based on some input. For example, the input may be from a timer tracking use of the tissue engineering device 602 over time in comparison to a beginning of use for a treatment regimen. As another example, the input may be a count—e.g., a counter tracking each energization of the tissue engineering device 602 over time at the given pulse frequency level (within an acceptable variance of that level, for example) and that count being compared to a specified number of times. As another example, the input may be sensor data—e.g., impedance monitor data that is compared to a specified threshold level (or levels) stored in a memory (or transmitted to an external, remote system for comparison to levels) to aid in a determination whether healing of the target tissue has reached a target level to transition to a different specified pulse frequency level identified in the same treatment regimen or a different treatment regimen.

If the treatment regimen specifies low pulse frequency, then the method 800 proceeds to block 810.

At block 810, the processor 202 (FIG. 2) of the tissue engineering device 602 generates the command for the low frequency pulse generator 210 (FIG. 2) to generate low pulse frequency pulses, such as in the example given in FIG. 3B and discussed above.

At block 812, the tissue engineering device 602's low frequency pulse generator 210 (FIG. 2) generates the PEMF (the pulses) according to the command(s) received from the processor 202 from block 810.

Returning to decision block 808, if the treatment regimen specifies high pulse frequency, then the method 800 instead proceeds to block 814.

At block 814, the processor 202 (FIG. 2) of the tissue engineering device 602 generates the command for the high frequency pulse generator 208 (FIG. 2) to generate high pulse frequency pulses, such as in the example given in FIG. 3A and discussed above.

At block 816 the tissue engineering device 602's high frequency pulse generator 208 (FIG. 2) generates the PEMF (the pulses) according to the command(s) received from the processor 202 from block 814.

From either block 810 or block 816, the method 800 proceeds to block 818.

At block 818, the tissue engineering device 602 tracks the time in use that PEMFs are generated for treatment of the indication (e.g., rotator cuff repair). This may be performed by the processor 202 (FIG. 2) with a timer function, or by polling a hardware timer separate from the processor 202 to name just a few examples.

At block 820, the tissue engineering device 602 compares the tracked time from block 818 against a total application time for the current periodic application (e.g., approximately 60 to 90 minutes for low pulse frequency PEMF signals and approximately 6 hours for high pulse frequency PEMF signals), such as may be stored as part of the treatment regimen in memory 204 (FIG. 2).

At decision block 822, if the tracked time from block 818 has not reached the time frame specified in the treatment regimen, then the method 800 returns to block 818 to continue tracking.

If the tracked time from block 818 has reached the time frame specified in the treatment regimen, then the method 800 proceeds to block 824.

At block 824, the tissue engineering device 602 deactivates the PEMF for the current periodic application (e.g., automatically; alternatively, a notification may be signaled to the user via the interface 610 which may include textual, audible, video, etc. information to the user). Deactivation may be of the PEMF signals only, or of powering down the entire tissue engineering device 602.

In some embodiments, the computing system is programmable and is programmed to execute processes including the processes of methods 500 and/or 700 discussed herein. Accordingly, it is understood that any operation of the computing system according to the aspects of the present disclosure may be implemented by the computing system using corresponding instructions stored on or in a non-transitory computer readable medium accessible by the processing system. For the purposes of this description, a tangible computer-usable or computer-readable medium can be any apparatus that can store the program for use by or in connection with the instruction execution system, apparatus, or device. The medium may include for example non-volatile memory including magnetic storage, solid-state storage, optical storage, cache memory, and Random Access Memory (RAM).

As a result of implementing the above-described approach, embodiments of the present disclosure improve the field of pulsed electromagnetic field therapy for tissue engineering, such as for tissue differentiation and/or tissue proliferation. In particular, embodiments of the present disclosure improve the efficacy of PEMF treatment for different indications beyond merely bone growth stimulation, and further that the PEMF treatment may be achieved via a combination of high pulse frequency PEMF (for proliferation) and low pulse frequency PEMF (for differentiation) in a manner that better promotes healing in a patient.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An apparatus, comprising:
an electromagnetic field transmitter configured to generate a pulsed electromagnetic field, the pulsed electromagnetic field having a slew rate comprising a ratio of change in amplitude of a magnetic field to a time to make the change in amplitude; and
a controller coupled to the electromagnetic field transmitter and configured to:
direct the slew rate of the pulsed electromagnetic field, wherein the slew rate comprises a value between 30 Tesla/second and 100 Tesla/second;
direct a pulse frequency of the pulsed electromagnetic field, wherein the pulse frequency comprises a value between 2 kilohertz and 6 kilohertz; and
maintain a treatment duration of the pulsed electromagnetic field according to a treatment regimen.

2. The apparatus of claim 1, wherein the treatment duration includes a time between 30 minutes and 3 hours.

3. The apparatus of claim 1, wherein the treatment regimen further includes a burst frequency comprising a value between 10 hertz and 20 hertz.

4. The apparatus of claim 1, wherein the treatment regimen further includes a periodicity of treatment, wherein the periodicity of treatment is one day.

5. The apparatus of claim 1, wherein the treatment regimen further includes a total duration of treatment between 2 weeks and 6 months.

6. The apparatus of claim 1, wherein the controller is further configured to direct an amplitude of the pulsed electromagnetic field, wherein the amplitude comprises a value between 5 milliTesla and 15 milliTesla.

7. The apparatus of claim 1, further comprising a sensor configured to monitor a progress of healing of musculoskeletal tissue during operation of the electromagnetic field transmitter.

8. The apparatus of claim 7, wherein the controller is further configured to select the pulse frequency in response to the progress of healing identified from the sensor.

9. An apparatus for tendon tissue repair, comprising:

a controller configured to maintain a slew rate of a pulsed electromagnetic field, the slew rate comprising a ratio of change in amplitude of a magnetic field to a time to make the change in amplitude, wherein the slew rate comprises a value between 30 Tesla/second and 100 Tesla/second, and wherein the pulsed electromagnetic field comprises a pulse frequency between 2 kilohertz and 6 kilohertz; and an electromagnetic field transmitter coupled to the controller and configured to generate the pulsed electromagnetic field with the slew rate and the pulse frequency for a treatment of musculoskeletal tissue.

10. The apparatus of claim 9, wherein a treatment duration for the treatment of the musculoskeletal tissue includes a time between 30 minutes and 3 hours.

11. The apparatus of claim 9, wherein a treatment regimen for the treatment of the musculoskeletal tissue further includes a burst frequency comprising a value between 10 hertz and 20 hertz.

12. The apparatus of claim 9, further comprising a sensor configured to monitor a progress of healing of the musculoskeletal tissue during operation of the electromagnetic field transmitter.

13. The apparatus of claim 12, wherein the controller is further configured to select the pulse frequency in response to the progress of healing identified from the sensor.

14. The apparatus of claim 9, wherein the controller is further configured to direct an amplitude of the pulsed electromagnetic field, wherein the amplitude comprises a value between 5 milliTesla and 15 milliTesla.

15. The apparatus of claim 9, wherein a treatment regimen for the treatment of the musculoskeletal tissue further includes a total duration of treatment between 2 weeks and 6 months.

16. A method for tendon tissue repair, comprising:

receiving, by a controller, an input identifying a treatment mode for application of a pulsed electromagnetic (EM) field (PEMF) to a tendon by an EM field generator;

sending, by the controller, a command to the EM field generator to generate a pulsed EM field in response to the input, the pulsed EM field having a slew rate comprising a value between 30 Tesla/second and 100 Tesla/second and a pulse frequency comprising a value between 2 kilohertz and 6 kilohertz; and directing, by the controller, the EM field generator to maintain the pulsed EM field with the slew rate and pulse frequency according to a treatment regimen.

17. The method of claim 16, wherein the treatment regimen includes a treatment duration between 30 minutes and 3 hours.

18. The method of claim 16, further comprising:

comparing, by the controller, a number of times that the EM field generator is energized to a threshold number; and deactivating, by the controller, the EM field generator in response to the number of times exceeding the threshold number.

19. The method of claim 16, wherein the tendon comprises a rotator cuff.

20. The method of claim 16, further comprising:

directing an amplitude of the pulsed EM field to a value between 5 milliTesla and 15 milliTesla.

* * * * *